United States Patent
Epperson

(10) Patent No.: US 10,639,392 B1
(45) Date of Patent: May 5, 2020

(54) SCENT MASKING COMPOSITION

(71) Applicant: Russell L. Epperson, Butler, MO (US)

(72) Inventor: Russell L. Epperson, Butler, MO (US)

(73) Assignee: SCENT THIEF, LLC, Overland Park, KS (US)

( * ) Notice: Subject to any disclaimer, the term of this patent is extended or adjusted under 35 U.S.C. 154(b) by 107 days.

(21) Appl. No.: 15/004,096

(22) Filed: Jan. 22, 2016

Related U.S. Application Data

(60) Provisional application No. 62/106,412, filed on Jan. 22, 2015.

(51) Int. Cl.
*A01M 1/00* (2006.01)
*A61L 9/013* (2006.01)

(52) U.S. Cl.
CPC .................................... *A61L 9/013* (2013.01)

(58) Field of Classification Search
None
See application file for complete search history.

(56) References Cited

U.S. PATENT DOCUMENTS

| | | | |
|---|---|---|---|
| 8,449,926 B2 | 5/2013 | Boegli | |
| 8,647,684 B2 | 2/2014 | Baube | |
| 2004/0064995 A1* | 4/2004 | Gilmore | A01M 31/008 43/1 |
| 2005/0019269 A1 | 1/2005 | Marks et al. | |
| 2006/0269509 A1 | 11/2006 | Gumbrecht et al. | |
| 2011/0318289 A1 | 12/2011 | Frodyma et al. | |
| 2012/0301421 A1 | 11/2012 | Hecking | |
| 2014/0352630 A1* | 12/2014 | Messina | A01N 49/00 119/712 |

FOREIGN PATENT DOCUMENTS

| | | |
|---|---|---|
| CN | 103720606 A | 4/2014 |
| WO | 2010019141 A1 | 2/2010 |

* cited by examiner

*Primary Examiner* — Dominic Lazaro
(74) *Attorney, Agent, or Firm* — Seyfarth Shaw LLP

(57) ABSTRACT

A scent-masking mixture and method for making and using that mixture are disclosed. That scent masking mixture includes an "Earth Scent" fragrance, eucalyptus essence, peppermint essence, rosemary essence, clove essence, and water. The majority of the scent-masking mixture may be water while the largest amount of active ingredient might be the "Earth Scent" fragrance. The scent-masking mixture beneficially includes equal amounts of eucalyptus essence and rosemary essence. Preferably there is more peppermint essence than clove essence.

19 Claims, No Drawings

SCENT MASKING COMPOSITION

RELATED APPLICATIONS

This application claims the benefit of U.S. Provisional Application No. 62/106,412, which was filed Jan. 22, 2015, the entire disclosures of which are incorporated herein by reference.

FIELD OF THE INVENTION

The presently disclosed subject matter is directed to masking scents. More particularly, it is directed to an odor-blocking mixture that is particularly well suited for masking scents during hunting or tracking game.

BACKGROUND OF THE INVENTION

Many game animals have highly developed senses of smell that are far more acute than that of humans No matter how well one may track a game animal, if the wind shifts towards the animal or if one gets close enough the animal can know you are there by your scent and quickly scurry away. Therefore, when hunting or tracking game it is imperative to reduce or to completely mask one's scent.

If view of the importance of reducing or masking one's scent a scent masking mixture is highly desirable. Ideally such a mixture would be both effective and economical. Given the desire to avoid harsh and potentially dangerous chemicals it would be beneficial if that mixture was natural. Ideally that mixture would either totally mask a wearer's scent or provide a scent that mimics that of the natural world. Preferably such a scent masking mixture could be provided in bulk quantities as either a liquid that is capable of being sprayed or as a semi-solid or solid such as a balm that can be easily spread.

SUMMARY OF THE INVENTION

The principles of the present invention provide for an effective, low cost mixture of natural ingredients that masks a user's scent or provides a scent that mimics that of the natural world. The inventive scent masking mixture can be provided in bulk quantities as either a sprayable liquid or as a semi-solid or solid that can be easily spread.

A scent-masking mixture in accord with the present invention includes an "Earth Scent" fragrance, eucalyptus essence, peppermint essence, rosemary essence, clove essence, and water. The majority of the scent-masking mixture may be water while the largest amount of active ingredient might be the "Earth Scent" fragrance. The scent-masking mixture beneficially includes equal amounts of eucalyptus essence and rosemary essence. Preferably there is more peppermint essence than clove essence.

A method of preparing a scent masking mixture in accord with the present invention includes combining an amount of eucalyptus oil, an amount of peppermint oil, an amount of rosemary oil, an amount of clove oil, an amount of an "Earth Scent" fragrance, and an amount of water in a vessel, mixing the ingredients in the vessel, heating the ingredients in the vessel until steam is detected, and allowing the ingredients in the vessel to cool. That method of preparing a scent masking mixture can further include the step of transferring the cooled ingredients into a spray bottle. Preferably heating occurs at less than two hundred fifty degrees Fahrenheit (250° F.), beneficially at approximately two hundred thirty degrees Fahrenheit (230° F.).

In addition, the method can include the steps of adding coconut oil to the ingredients, adding beeswax to the ingredients, mixing the resulting mixture over medium heat until the appearance of steam vapors, removing the resulting mixture from heat, allowing the resulting mixture to solidify, and then cutting the resulting solid mixture into desired portions.

A solid version of a scent masking mixture according to the present invention can be made by combining eucalyptus oil, peppermint oil, rosemary oil, clove oil, an "Earth Scent" fragrance, coconut oil, beeswax, and water in a vessel, mixing the ingredients in the vessel, heating the ingredients in the vessel, and cooling the ingredients to allow them to solidify. The solid scent masking mixture can then be cut into portions. Beneficially heating occurs at less than two hundred fifty degrees Fahrenheit (250° F.), preferably at approximately two hundred thirty degrees Fahrenheit (230° F.).

DETAILED DESCRIPTION OF THE PREFERRED EMBODIMENT

What follows are descriptions of the components of a scent masking mixture, how to make that scent-masking mixture, and how to use that scent-masking mixture. However, the invention is not limited to what is specifically described. A person skilled in the art will appreciate that many other embodiments of the invention are possible without deviating from the basic concept of the invention. Any such work around will also fall under the scope of this invention.

The terms "a" and "an" as used herein do not denote a limitation of quantity, but rather denote the presence of at least one of the referenced items.

The present invention describes a scent masking mixture that can be prepared and used as subsequently described. The preferred scent-masking mixture can be fabricated as a sprayable liquid using the following components:

| Component | Amount |
| --- | --- |
| "Earth Scent" fragrance (beneficially water-based) | 1 oz. |
| Eucalyptus essence | 40 drops |
| Peppermint essence | 20 drops |
| Rosemary essence | 40 drops |
| Clove essence | 10 drops |
| Water | 14 oz. |

Thus the largest component of the mixture is water. The largest amount of active ingredient is the "Earth Scent" fragrance, followed by substantially equal amounts of Eucalyptus essence and Rosemary essence. There is more Peppermint essence than Clove essence.

The various essences can be purchased on the open market or extracted from base plants using any number of extraction techniques such as steam distillation, water distillation, expression, enfleurage, solvent extraction or any number of other techniques.

A suitable "Earth Scent" is available from Royal Supreme Foods Inc., Lakewood, N.J. Other suitable "Earth Scents" are readily available on the open market. The proper "Earth Scent" will depend on the location in which the mixture will be used as well as being tailored, such as by experience and trial and error, to the game being hunted or tracked.

Each fluid drop is understood as being a drop from a standard straight glass pipette type dropper such as those manufactured by Scientific Equipment of Houston or equivalent. There are about five-hundred ninety-one drops per fluid ounce of water (591 drop/fl. oz.).

Given the foregoing components the proper post-processing of the scent-masking mixture is very important and preferably should be performed as given below:

Placing all of the components into a heat-resistant vessel.

Mixing the components over a heat source to a temperature of less than 250° F. and preferably at approximately two-hundred thirty degrees Fahrenheit (230° F.) until the initial appearance of steam vapors.

Removing the vessel from the heat source.

Allowing mixture to cool.

The scent-masking mixture at this stage is a liquid that can be transferred to another container such as a spray bottle. In fact, the preferred dispensation method is to use it as a spray from a spray bottle.

An alternative embodiment of the present invention takes the form of a solid scent-masking mixture. Obtaining a solid version of a scent-masking mixture according to the present invention may be achieved by performing the following additional processing steps.

Having the foregoing liquid mixture in a heat-resistant vessel.

Adding four ounces (4 oz.) of coconut oil.

Adding two tablespoons (2 Tbsp.) of beeswax.

Mixing the resulting mixture over medium heat until the appearance of steam vapors.

Removing the resulting mixture from heat.

Allowing the resulting mixture to cool and solidify.

Cutting and dividing the resulting solid scent-masking mixture into desired portions.

It is envisioned that other styles and configurations of the present invention can be easily incorporated into the teachings of the present invention, and while only two embodiments are described that is for the purposes of clarity and disclosure and not by way of limitation of scope.

The preferred embodiment of the present invention can be utilized by the common user in a simple and effortless manner with little or no training. Purchase or otherwise obtain the scent-masking mixture. The scent-masking mixture is envisioned as being made available where hunting supplies and consumer air freshener products are typically sold. After initial purchase the application of the scent-masking mixture is as follows: identifying surfaces to be treated with the scent-masking mixture such as clothing, traps, animals, various surfaces, and the like; using the spray bottle to manually apply the scent-masking mixture in an expected airborne manner; and, benefiting from a scent masking mixture which masks unwanted scents while enjoying hunting, trapping, and the like.

The sprayable liquid scent-masking mixture is understood to be especially useful for hunting or trapping. However, additional uses of the scent-masking mixture may include masking the scent of animals to provide protection during a period of estrus; masking various household odors; and masking the animal odors of pets or other animals.

The solid embodiment of the scent-masking mixture may be utilized by positioning a quantity of the solid scent-masking mixture at an indoor and/or outdoor location to initiate airborne emission of the corresponding masking odor to mask local airborne scents, as desired.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A scent-masking composition comprising:
   a water-based East Scent fragrance;
   eucalyptus essence;
   peppermint essence;
   rosemary essence;
   clove essence; and
   water;
   wherein combining the water-based Earth Scent fragrance, eucalyptus essence, peppermint essence, roesmary essence, clove essence, and water with heating at a temperature of less than 250° F. until steam is detected forms the liquid sent-masking composition.

2. The scent-masking composition of claim 1, wherein the majority of said mixture is water.

3. The scent-masking composition of claim 2, wherein the largest amount of active ingredients is Earth Scent fragrance.

4. The scent-masking composition of claim 3, wherein the second largest amount of active ingredients are eucalyptus essence and rosemary essence.

5. The scent-masking composition of claim 4 containing substantially equal amounts of eucalyptus essence and rosemary essence.

6. The scent-masking composition of claim 5 in which there is more peppermint essence than clove essence.

7. A scent-masking composition comprising:
   a water-based East Scent fragrance;
   eucalyptus essence;
   peppermint essence;
   rosemary essence;
   clove essence
   coconut oil;
   beeswax; and
   water;
   wherein combining the water-based Earth Scent fragrance, eucalyptus essence, peppermint essence, roesmary essence, clove essence, and water with heating at a temperature of less than 250° F. until steam is detected forms the liquid sent-masking composition.

8. The scent-masking composition of claim 7, wherein the majority of said mixture is water.

9. The scent-masking composition of claim 8, wherein the largest amount of active ingredients is Earth Scent fragrance.

10. The scent-masking composition of claim 9, wherein the second largest amount of active ingredients are eucalyptus essence and rosemary essence.

11. The scent-masking composition of claim 10 containing substantially equal amounts of eucalyptus essence and rosemary essence.

12. The scent-masking composition of claim 11 in which there is more peppermint essence than clove essence.

13. A method of preparing a scent masking composition according to claim 1 comprising the steps of:
   combining ingredients comprising an amount of eucalyptus oil, an amount of peppermint oil, an amount of rosemary oil, an amount of clove oil, an amount of a water-based Earth Scent fragrance;
   mixing the ingredients in a vessel;
   heating the ingredients in the vessel at a temperature of less than 250° F. until steam is detected;
   adding an amount of water into the vessel; and
   allowing the ingredients and water in the vessel to cool.

14. The method of preparing a scent masking composition according to claim 13, further including the step of transferring the cooled ingredients and water into a spray bottle.

15. The method of preparing a scent masking composition according to claim 13, wherein the heating step occurs at approximately 230 degrees Fahrenheit.

16. The method of preparing a scent masking composition according to claim 13, further including the steps of:
   adding coconut oil to the ingredients;
   adding beeswax to the ingredients;
   allowing the heated mixture of ingredients and water to solidify by cooling in order to form a solid mixture; and
   cutting the solid mixture into portions.

17. A method of preparing a scent masking composition according to claim 7 comprising the steps of:
   combining ingredients comprising eucalyptus oil, peppermint oil, rosemary oil, clove oil, a water-based Earth Scent fragrance, coconut oil, beeswax, and water in a vessel;
   mixing the ingredients in the vessel;
   heating the ingredients in the vessel at a temperature of less than 250° F. until steam is detected; and
   cooling the ingredients in order to solidify.

18. The method of preparing a scent masking composition according to claim 15, further including the steps of:
   allowing the heated mixture of ingredients and water to solidify by cooling in order to form a solid mixture; and
   cutting the solid mixture into portions.

19. The method of preparing a scent masking composition according to claim 17, wherein heating occurs at approximately 230 degrees Fahrenheit.

\* \* \* \* \*